(12) United States Patent
Sedlet

(10) Patent No.: US 7,446,522 B2
(45) Date of Patent: Nov. 4, 2008

(54) CONSTANT CONTACT WHEEL FOR CLOSE INTERVAL SURVEY DEVICES

(76) Inventor: Paul J. Sedlet, 10487 N. 91st Ave., #6, Peoria, AZ (US) 85345

( * ) Notice: Subject to any disclaimer, the term of this patent is extended or adjusted under 35 U.S.C. 154(b) by 619 days.

(21) Appl. No.: 11/082,413

(22) Filed: Mar. 17, 2005

(65) Prior Publication Data

US 2005/0212518 A1    Sep. 29, 2005

Related U.S. Application Data

(60) Provisional application No. 60/556,977, filed on Mar. 26, 2004.

(51) Int. Cl.
  *G01R 31/02* (2006.01)
  *G01N 27/00* (2006.01)
  *G01V 3/00* (2006.01)
(52) U.S. Cl. .................. 324/72; 324/71.1; 324/347; 324/348
(58) Field of Classification Search ............... 324/71.1, 324/72, 347, 348
  See application file for complete search history.

(56) References Cited

U.S. PATENT DOCUMENTS

| 2,105,247 | A |   | 1/1938  | Jakosky |          |
|-----------|---|---|---------|---------|----------|
| 2,974,276 | A | * | 3/1961  | Davis   | 324/72   |
| 4,258,323 | A | * | 3/1981  | Andrews et al. | 324/348 |
| 4,388,594 | A | * | 6/1983  | Deskins et al. | 324/72 |
| 4,414,511 | A | * | 11/1983 | Waits et al. | 324/71.1 |
| 4,584,530 | A | * | 4/1986  | Nicholson | 324/72 |
| 5,171,692 | A | * | 12/1992 | Craig, Jr. | 205/790 |

FOREIGN PATENT DOCUMENTS

| EP | 85303193.8 | 3/1985 |
| GB | 843419     | 8/1960 |
| GB | 2 157 441 A | 10/1985 |
| GB | 2 224 852 A | 5/1990 |

\* cited by examiner

*Primary Examiner*—Timothy J Dole
(74) *Attorney, Agent, or Firm*—Parsons & Goltry; Robert A. Parsons; Michael W. Goltry

(57) ABSTRACT

A constant contact reference wheel system includes a vehicle carrying a water reservoir, and a constant contact reference wheel. The constant contact reference wheel includes a frame having a first end and a second end, an attachment mechanism carried by the first end removably coupling the frame to the vehicle, a wheel structure having a rim for rolling contact with a soil surface, and a reference cell carried by the frame. A water pathway extends from the water source to the rim. The rim exudes water for contact with the soil surface, and the reference cell is in fluid communication with the water pathway.

17 Claims, 3 Drawing Sheets

US 7,446,522 B2

CONSTANT CONTACT WHEEL FOR CLOSE INTERVAL SURVEY DEVICES

CROSS-REFERENCE TO RELATED APPLICATION

This application claims the benefit of U.S. Provisional Application No. 60/556,977, filed 26 Mar. 2004.

FIELD OF THE INVENTION

This invention relates to close interval soil potential measurement devices.

More particularly, the present invention relates to devices for determining the effectiveness of cathodic protection for pipelines.

BACKGROUND OF THE INVENTION

Metallic pipes used in pipelines for transporting fluids, gasses, etc. and transmission lines are found abundantly throughout the world. These metallic pipes or conduits, such as ductile iron pipes, are used as water mains and the like. While effective, metallic pipelines have a corrosion problem, when immersed in an electrolyte. A current is created between the metal and the electrolyte causing ions to leave the metal. Many untold miles of pipelines are buried in soil, which is an effective electrolyte. Over time, the metal of the pipeline can be weakened, resulting in leaks and breakages. Various forms of cathodic protection are employed to slow or if possible, halt the corrosion of pipelines. Corroding metal is anodic relative the cathodic or non-corroding areas. Cathodic protection simply couples a metal of higher potential to the metal of the pipeline, creating an electrochemical cell in which the metal of the pipeline becomes a cathode and no longer loses ions. In theory, this practice is a complete cure to corrosion. However, in application many problems can occur, including expense and technical difficulties. However, it is clear that knowing the level of protection, or lack thereof is important.

The primary measurement to determine the effectiveness of cathodic protection is a pipe-to-soil potential criterion. This technique measures the voltage difference between the pipeline and a reference electrode, typically a copper-copper sulfate electrode, placed in or on the electrolyte near the structure. Test stations are often periodically placed along the pipeline to measure the potential of the pipeline and the surrounding soil. These test stations, however, are generally widely separated, and do not give measurements for areas between the stations. This problem has been partially overcome by the use of hand held probes and a wire dispenser carried by a backpack. The wire is coupled to a test station to maintain a measurement of the potential of the pipeline, while the hand probe is periodically placed in contact with the ground to obtain the soil potential, which can then be compared to the pipe potential. This gives more measurements than the test stations, but can be time consuming and tiring to the individual performing the measurements.

It would be highly advantageous, therefore, to remedy the foregoing and other deficiencies inherent in the prior art.

Accordingly, it is an object of the present invention to provide a new and improved method and apparatus for measuring pipe-to-soil potential.

SUMMARY OF THE INVENTION

Briefly, to achieve the desired objects of the present invention in accordance with a preferred embodiment thereof, provided is a constant contact reference wheel system including a frame having a first end and a second end. A wheel structure having a rim for rolling contact with a soil surface is rotatably carried proximate the second end of the frame. A reference cell is carried by the frame. An electrically conductive pathway extends from the rim to the reference cell.

In a specific aspect of the invention, the electrically conductive pathway includes a water pathway extending from a water source to the rim. The rim exudes water for contact with the soil surface, and the reference cell is in fluid communication with the water pathway. The rim includes at least one opening for egress of water therefrom. In another aspect, the wheel structure includes a water permeable material extending around an outer periphery of the rim for receiving water from the at least one opening of the rim, forming a constant contact with the soil surface. The wheel structure further includes a hub and at least one spoke coupling the hub to the rim. The water pathway extends from the water source through the hub and through the at least one spoke to the rim. In yet another aspect, a soil pre-water outlet is positioned intermediate the first end and the wheel structure and coupled to the water source for wetting the soil surface in front of the wheel.

In another embodiment, a constant contact reference wheel system includes a vehicle carrying a water reservoir and a constant contact reference wheel. The constant contact reference wheel includes a frame having a first end and a second end, and an attachment mechanism carried by the first end removably coupling the frame to the vehicle.

Also provided is a method of providing constant electrical contact with a soil surface. The method includes providing a constant contact reference wheel system, injecting water into the water pathway, rolling the wheel structure over the soil surface, and sensing voltage potentials from the soil surface through the water pathway by the reference cell.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF THE PREFERRED EMBODIMENT

Metallic pipelines buried in soil often have problems with corrosion. The corrosion can be controlled by the use of cathodic protections of one sort or another. Monitoring of the cathodic protection is accomplished using a reference electrode to determine the soil potential, and a test station electrode providing the pipe potential. The difference of those measurements, are calculated for each survey location to determine the cathodic protection for that spot using the pipe-to-soil criteria.

Figure 1:
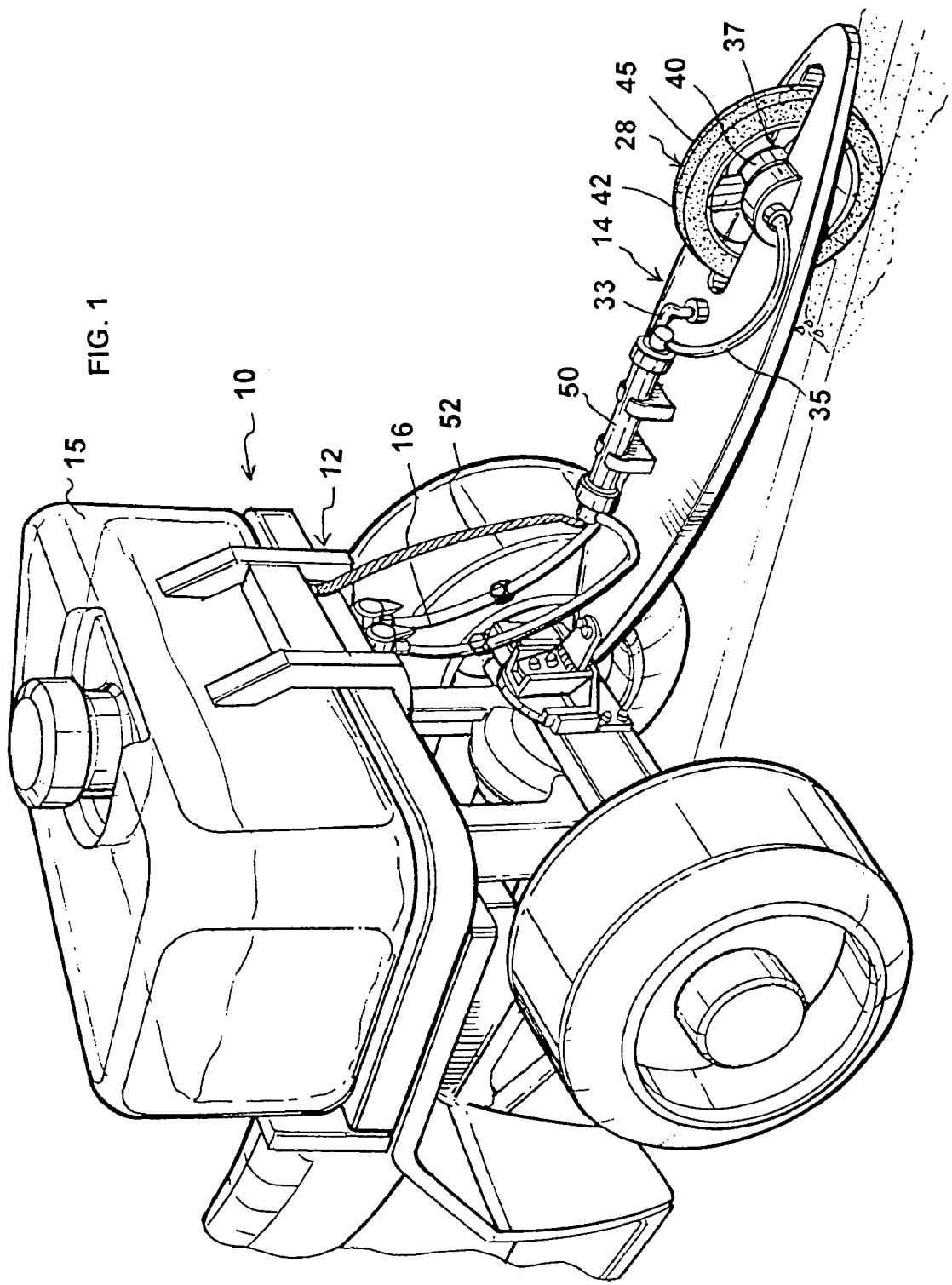
FIG. 1 is a partial side view of an automated close interval survey vehicle with contact wheel according to the present invention.

Turning now to the drawings in which like reference characters indicate corresponding elements throughout the several views, attention is first directed to FIG. 1 which illustrates an automatic close interval survey vehicle generally designated 10. Vehicle 10 can be substantially any vehicle, such as a truck, but preferably includes an all terrain vehicle (ATV) 12 of conventional design, pulling a constant contact reference wheel system 14 and carrying a wire dispensing device (not shown) coupled to constant contact reference wheel system 14. Vehicle 10 also includes a water reservoir 15 mounted on ATV 12 and a conduit 16 with a valve coupled thereto.

Figure 2:
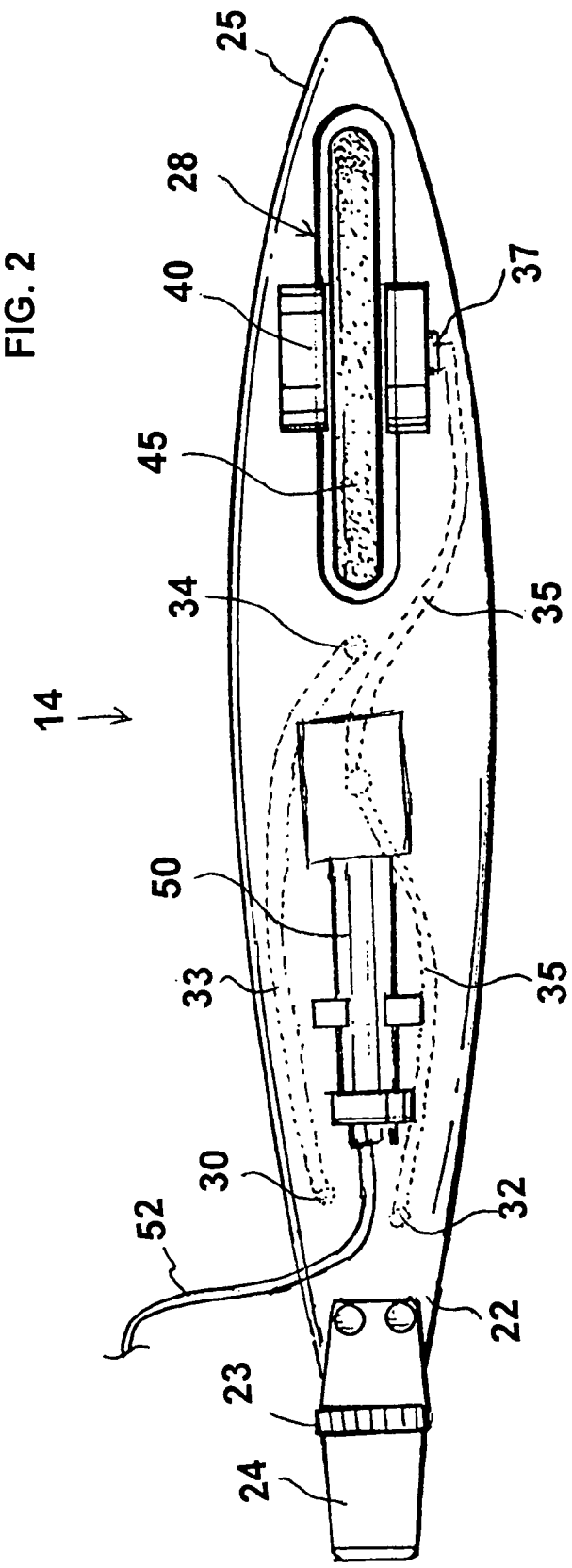
FIG. 2 is a top view of a constant contact reference wheel of the vehicle of FIG. 1.
Figure 3:
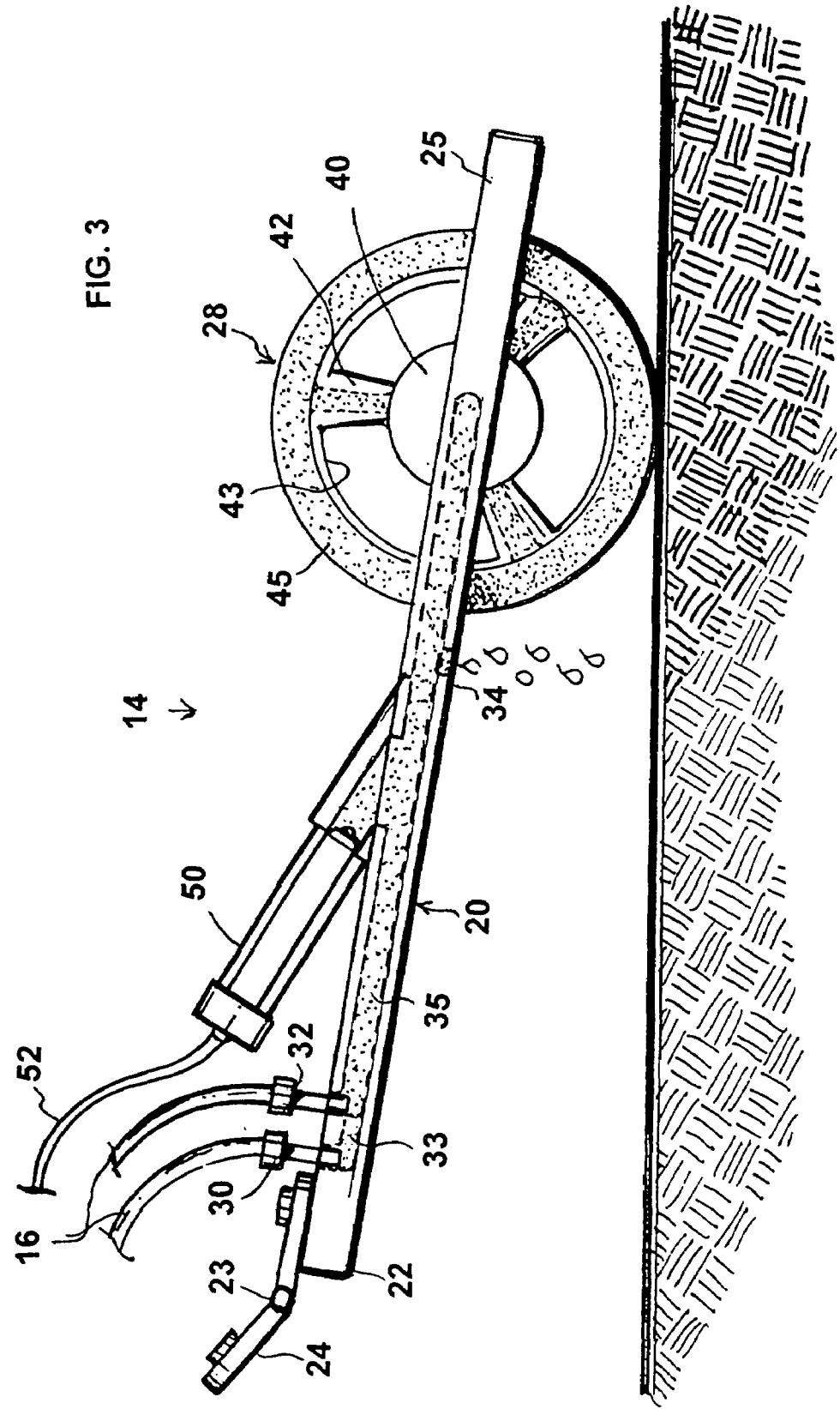
FIG. 3 is a side view of a constant contact reference wheel.

With additional reference to FIGS. 2 and 3, constant contact reference wheel system 14 includes a substantially rigid frame 20 having an end 22 and an end 25. End 22 is coupled to ATV 12 by a biased coupling, which in this embodiment is a biased hinge 23 and bracket 24. End 25 preferably terminates in a bifurcation or slot. The bifurcation or slot rotatably receives a wheel structure 28. Water conduit 16 couples reservoir 15 to a soil pre-water inlet 30 and reference water pathway inlet 32. Single or Multiple conduits 16 can couple single or multiple reservoirs 15 to inlets 30 and 32. Inlets 30 and 32 couple reservoir 15 to a soil pre-water conduit 33 terminating in a soil pre-water outlet 34, and a reference water conduit 35, respectively. Conduits 33 and 35 can be hoses, pipes or the like attached to frame 20, or, as illustrated in FIGS. 2 and 3, formed in frame 20. Pre-water outlet 34 is positioned on frame 20 forward (toward vehicle) of wheel structure 28, generally intermediate end 22 and wheel structure 28. Outlet 34 is used to wet the soil at the test location if needed, as will be described presently.

Reference water conduit 35 terminates at a rotational fitting 37 at end 25. Wheel structure 28 is mounted for rotation by a hub 40 to end 25 within the slot or bifurcation. Hub 40 receives water from conduit 35 through rotational fitting 37. Wheel structure 28 includes a plurality of spokes 42 extending from hub 40 and terminating in a rim 43. Spokes 42 are hollow to allow water from hub 40 to flow to rim 43. Openings in rim 43 permit water flow to an outer surface thereof. A water permeable material, such as a soaker tube 45 or similar material receives water from spokes 42 and becomes soaked around the entire periphery of rim 43. Thus, a water pathway is formed from contact with the ground through spokes 42 to hub 40 and through conduit 35 to a reference cell 50 carried by frame 20 and in contact with the water pathway. The components in the water pathway, such as frame 20, conduits 35, rim 43 and spokes 42, etc. are non-conductive. The presence of water from reservoir 15 completes a conductive water pathway to reference cell 50. In this manner, a constant contact is provided between reference cell 50 and the ground as long as a water pathway is formed by water in system 14. Hinge 23 is biased to hold frame 20 down toward the ground, so wheel structure 28 remains in contact with the ground even over uneven features. One skilled in the art will recognize that a biased coupling can include a flexible coupling with a weight carried proximate end 25, biasing frame 20 towards the ground. A lead wire 52 extends from reference cell 50 to a data logger for receiving and storing the survey data.

Data from the test station is received over a dispensing wire carried by a spool, and coupled to the data logger. As the wire is dispensed, a wire measurer measures the distance traversed. A controller is provided to receive the distance data, and trigger the data logger at a predetermined distance. In this manner, as ATV 12 is driven over the pipeline, a soil potential can be automatically taken at predetermined intervals without stopping the vehicle. It will be understood that dispensing wire can be removably mounted such as with a spool carried by ATV 12, or a permanent housing can be mounted instead.

As wire is dispensed, survey events occur as triggered by the controller set for specific distances as measured by the wire measurer or manually by the operator. Additionally, if conditions, such as an arid environment, warrant, as the survey events occur, water is released from water reservoir 15 carried on ATV 12 through soil pre-water conduit 33 that terminates at outlet 34. This application of water to the soil before wheel structure 28 enhances the contact between the reference cell electrode and the ground, through soaker hose 45. It will be understood that the timing of the release of water is such that water is released on the area where wheel structure will pass as the data logger is triggered. This can be controlled by actuating a solenoid to open the valve coupled to conduit 16 upon the proper signal.

As ATV 12 is driven along the pipeline, wire coupled to a test station is dispensed from the vehicle. Manually actuated testing can be employed, or other automatic actuating can be used, such as the wire being pulled through a wire measurer. A distance signal is generated and transmitted to the controller. At a specified distance, the data logger is triggered to initiate a test, and if necessary, the water valve is opened to wet the ground to be tested an interval before the trigger. The controller triggers a test event automatically using wheel structure 28.

Various changes and modifications to the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. A constant contact reference wheel system comprising:
   a frame having a first end and a second end;
   a wheel structure having a rim for rolling contact with a soil surface, the wheel rotatably carried proximate the second end of the frame;
   a water permeable non-absorbent material extending around an outer periphery of the rim, the water permeable non-absorbent material receiving water from the rim for forming a constant contact with the soil surface;
   a reference cell carried by the frame; and
   an electrically conductive pathway extending from the water permeable non-absorbent material to the reference cell, the electrically conductive pathway is a water pathway extending from a water source to the rim, the water permeable non-absorbent material exuding water for contact with the soil surface, the reference cell being in fluid communication with the water pathway.

2. A system as claimed in claim 1 wherein the rim includes at least one opening for egress of water therefrom.

3. A system as claimed in claim 2 wherein the wheel structure further includes a hub and at least one spoke coupling the hub to the rim, the water pathway extending from the water source through the hub and through the at least one spoke to the rim.

4. A system as claimed in claim 1 further including a soil pre-water outlet positioned intermediate the first end and the wheel structure and coupled to the water source for wetting the soil surface in front of the wheel.

5. A constant contact reference wheel system comprising:
a vehicle carrying a water reservoir;
a constant contact reference wheel including:
- a frame having a first end and a second end;
- an attachment mechanism carried by the first end removably coupling the frame to the vehicle;
- a wheel structure having a rim for rolling contact with a soil surface, the wheel rotatably carried proximate the second end of the frame;
- a water permeable non-absorbent material extending around an outer periphery of the rim, the water permeable non-absorbent material receiving water from the rim for forming a constant contact with the soil surface;
- a reference cell carried by the frame; and
- a water pathway extending from the water reservoir to the water permeable non-absorbent material, the water permeable non-absorbent material exuding water for contact with the soil surface, the reference cell in fluid communication with the water pathway.

6. A system as claimed in claim 5 wherein the rim includes at least one opening for egress of water therefrom.

7. A system as claimed in claim 6 wherein the wheel structure further includes a hub and at least one spoke coupling the hub to the rim, the water pathway extending from the water reservoir through the hub and through the at least one spoke to the rim.

8. A system as claimed in claim 5 further including a soil pre-water outlet positioned intermediate the first end and the wheel structure and coupled to the water reservoir for wetting the soil surface in front of the wheel.

9. A system as claimed in claim 8 further including a conduit extending from the water reservoir to the soil pre-water outlet, the conduit controlled by a valve having an open position and a closed position.

10. A system as claimed in claim 5 further including a data logger coupled to the reference cell for receiving and storing data therefrom.

11. A system as claimed in claim 5 wherein the attachment mechanism includes a biased coupling for biasing the frame downwardly.

12. A method of providing constant electrical contact with a soil surface comprising the steps of:
- providing a constant contact reference wheel system including a frame having a first end and a second end, a wheel structure having a rim, a water permeable non-absorbent material extending around an outer periphery of the rim in rolling contact with the soil surface, the wheel rotatably carried proximate the second end of the frame, a reference cell carried by the frame, and a water pathway extending from a water source through the water permeable non-absorbent material to the soil surface, the water permeable non-absorbent material exuding water for contact with the soil surface, the reference cell in fluid communication with the water pathway;
- injecting water into the water pathway;
- rolling the wheel structure over the soil surface; and
- sensing voltage potentials from the soil surface through the water pathway by the reference cell.

13. A method as claimed in claim 12 wherein the step of providing further includes providing the rim with at least one opening for egress of water therefrom.

14. A method as claimed in claim 13 wherein the step of providing further includes providing the wheel structure with a hub and at least one spoke coupling the hub to the rim, the water pathway extending from the water source through the hub and through the at least one spoke to the rim.

15. A method as claimed in claim 12 further including providing a soil pre-water outlet carried by the frame and positioned intermediate the first end and the wheel structure, coupling the soil pre-water outlet to the water source, and wetting the soil surface in front of the wheel prior to a test.

16. A method as claimed in claim 12 wherein the step of rolling the wheel structure over the soil surface includes the step of coupling the first end of the frame to a vehicle.

17. A method as claimed in claim 16 further including the step of biasing the wheel structure against the soil surface.

* * * * *

UNITED STATES PATENT AND TRADEMARK OFFICE
Certificate

Patent No. 7,446,522 B2                                          Patented: November 4, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Paul J. Sedlet, Peoria, AZ (US); and Bryan Evan Reed, Camp Verde, AZ (US).

Signed and Sealed this Third Day of May 2011.

MELISSA J. KOVAL
*Supervisory Patent Examiner*
Art Unit 2858
Technology Center 2800